(12) United States Patent
Chang

(10) Patent No.: US 10,363,335 B2
(45) Date of Patent: Jul. 30, 2019

(54) DISPOSABLE GAS DIFFUSION DEVICE

(71) Applicant: Guangzhou Faner Aroma Product Co., Ltd., Guangzhou (CN)

(72) Inventor: Hsu-Hui Chang, Guangzhou (CN)

(73) Assignee: GUANGZHOU FANER AROMA PRODUCT CO., LTD., Guangzhou, Guangdong (CN)

(*) Notice: Subject to any disclaimer, the term of this patent is extended or adjusted under 35 U.S.C. 154(b) by 325 days.

(21) Appl. No.: 15/294,800

(22) Filed: Oct. 17, 2016

(65) Prior Publication Data

US 2018/0104373 A1  Apr. 19, 2018

(51) Int. Cl.
*B05B 7/00* (2006.01)
*A61L 9/14* (2006.01)
*B05B 7/24* (2006.01)

(52) U.S. Cl.
CPC ............ *A61L 9/145* (2013.01); *B05B 7/0012* (2013.01); *B05B 7/2429* (2013.01)

(58) Field of Classification Search
CPC ....... B05B 7/0012; B05B 7/04; B05B 7/0416; B05B 7/0483; B05B 7/2405; B05B 7/2421; B05B 7/2424; B05B 7/2429; B05B 7/2437; A61L 9/145
USPC ........ 239/310, 311, 318, 337, 338, 339, 340
See application file for complete search history.

(56) References Cited

U.S. PATENT DOCUMENTS

| | | | |
|---|---|---|---|
| 1,191,617 A * | 7/1916 | Ruete | F16L 33/02 24/19 |
| 7,878,418 B2 * | 2/2011 | Sevy | A61M 11/06 128/200.18 |
| 9,248,461 B2 * | 2/2016 | Ansley | B01F 5/0413 |
| 9,421,295 B1 * | 8/2016 | Li | A61L 9/125 |
| 9,517,286 B1 * | 12/2016 | Li | A61L 9/145 |
| 9,895,464 B2 * | 2/2018 | Sevy | A61L 9/14 |
| 2018/0141063 A1 * | 5/2018 | Tsai | B05B 7/2405 |

* cited by examiner

*Primary Examiner* — Jason J Boeckmann
(74) *Attorney, Agent, or Firm* — Leong C. Lei

(57) ABSTRACT

A disposable gas diffusion device includes a gas supply device, which includes therein a gas inlet device, which includes a coupling section, and a compression element. The coupling section includes therein a gas conveyance hole. A container has an end connected to a diffuser that is provided with a gas entrance passage having an opposite end extending to a bottom of the diffuser. The bottom of the diffuser is provided with a liquid guiding device, which has an opposite end extending to a location adjacent to a bottom of the container. The diffuser has a top end in which an exit opening is formed. The gas supply device is operable to guide a pressurized gas into the container on induce a negative pressure zone inside the container in order to convey a liquid through the liquid guiding device to an atomization hole to be atomized and sprayed out.

13 Claims, 10 Drawing Sheets

DISPOSABLE GAS DIFFUSION DEVICE

TECHNICAL FIELD OF THE INVENTION

The present invention relates generally to a disposable gas diffusion device, and more particularly to a gas diffusion device that is operable to introduce a pressurized gas from a gas supply device into a container and induces a negative pressure zone inside the container so that through an operation based on high/low pressures, a liquid is conducted and conveyed through a liquid guiding device upward to an atomization hole, whereby due to the conveyance speed of the liquid being relatively high, the liquid, when passing though the atomization hole, is immediately sprayed out to form a mist and the atomized liquid is discharged through an exit opening to thereby achieve automatic atomization and spraying and easy disassembling.

DESCRIPTION OF THE PRIOR ART

The progress of technology and science makes modern technical products convenient in use and also guides modern people to pay increasing attention to material life and spiritual life. Building a comfortable living environment is becoming a goal sought by modern people. To provide refresh air that carries no odor smells and contaminants to the living environment in order to maintain good spiritual condition and increase working performance, it is commonplace to use an aromatic spray that comprises a container holding therein an aromatic fluid that can be atomized and sprayed in air for eliminating indoor odorant smells and thus, a comfortable living environment can be achieved.

To ease the use of the aromatic sprays by users, automatic aromatic sprays, which may automatically conducts an operation of atomizing and spraying aromatics, are available. The conventional automatic aromatic sprays comprises a motor that is operatively coupled to an eccentric cam so that when the motor rotates, the eccentric cam is driven to depress a nozzle mounted to an aromatic container such that the nozzles sprays out the aromatic. The conventional nozzles that are combined with the aromatic containers must be operated with a relatively large instantaneous pressing force in order to atomize the aromatic fluid for subsequently spraying. The eccentric cam arrangement that is adopted in the conventional automatic aromatic sprays is generally incapable of providing a sufficient force for such a depressing operation so that the aromatic fluid so sprayed out has not been fully atomized and may be in the form of small liquid droplets, leading to a severe drawback in the operation thereof.

In view of the above, the present invention aims to provide a disposable gas diffusion device that helps improve the convenience of use by users and overcomes the drawbacks of the prior art.

SUMMARY OF THE INVENTION

To achieve the above object, the present invention provides a disposable gas diffusion device, which generally comprises a gas supply device, which is provided, in an interior thereof, with a gas inlet device and a compression element, the gas inlet device being provided, at one side thereof, with a gas inlet section and being also provided, at another side thereof, with a gas outlet section, the gas outlet section having an end connected to the compression element, the gas supply device being provided, at one side thereof, with a coupling section, the coupling section being provided, in an inside thereof, with a gas conveyance hole, the gas conveyance hole being connected to one end of the compression element; and a diffusion device, which is connected to the coupling section, the diffusion device comprising a container and a diffuser, the container having an end connected to a circumference of the diffuser to allow a bottom of the diffuser to be received in an interior of the container, the diffuser having a circumference that is provided with a gas entrance section, the gas entrance section having one side that is provided with a gas entrance passage, the gas entrance passage being in tight connection with the gas conveyance hole, the gas entrance passage having an end arranged at a side of the gas entrance section, the gas entrance passage having another end extending to a bottom of the diffuser, the diffuser being provided, in the bottom thereof, with a liquid guiding device, the liquid guiding device having an end connected to the bottom of the diffuser, the liquid guiding device having another end extending to a location adjacent to a bottom of the container, the liquid guiding device having a circumference in which an atomization hole is formed, the atomization hole having an end communicating with the liquid guiding device, the atomization hole having another end arranged at a location adjacent to another end of the gas entrance passage, the diffuser having a circumference connected to the coupling section, the gas conveyance hole being in tight connection with the gas entrance passage, the diffuser having a top end that is provided with an exit opening.

In the above-described coupling section, the coupling section has a circumference that is connected to a retention device, the retention device has an end pivotally connected to one side of the coupling section, the retention device having another end engaging and retained by another side of the coupling section to retain the diffuser between the coupling section and the retention device.

In the above-described coupling section, the coupling section is provided, in another side, with a retention trough for engaging and retaining another end of the retention device.

In the above-described diffuser, the diffuser has a circumference that is provided with a retention section, the retention section being in engagement with and retained by the retention device to have the diffuser retained between the retention device and the coupling section.

In the above-described diffuser, the diffuser is provided, in an interior thereof, with a slow flowing device for reducing a speed of a pressurized gas and filtering off large particles of atomized liquid.

In the above-described gas supply device, the gas supply device is provided, in an interior thereof, with a flow driving device, the gas supply device having a circumference that is provided with at least one air ingress opening, whereby when the flow driving device is put in operation, external gas is first drawn in through the air ingress section and the gas is then blown to one side of the gas supply device so that gas fed out through the exit opening is blown further by the gas blown out of the flow driving device.

In the above-described gas supply device, the gas supply device is provided, on one side thereof, with a control section so that the control section controls flow rate and time interval of spraying gas by the gas supply device.

In the above-described gas supply device, the gas supply device has a circumference to which an electrical wire is connected so that electrical power is supplied through the electrical wire to the gas supply device and the gas supply device is provided, in an interior thereof, with a power supply device so that the power supply device supplies electrical power to the gas supply device in case of power failure.

In the above-described gas entrance section, the gas entrance section is a gas entrance section in the form of an inclined surface to facilitate tight connection between the gas entrance section and the gas conveyance hole so that the gas entrance passage is kept in tight connection with the gas conveyance hole.

In the above-described gas entrance section, the gas entrance passage has one end having a diameter that is greater than a diameter of another end of the gas entrance passage.

In the above-described gas inlet section, the gas inlet section is coupled to a sponge for filtering off impurities entraining external air.

In the above-described container, the container receives and holds therein a liquid and the liquid comprises perfume, disinfection liquid, or insect expellant liquid.

The foregoing objectives and summary provide only a brief introduction to the present invention. To fully appreciate these and other objects of the present invention as well as the invention itself, all of which will become apparent to those skilled in the art, the following detailed description of the invention and the claims should be read in conjunction with the accompanying drawings. Throughout the specification and drawings identical reference numerals refer to identical or similar parts.

Many other advantages and features of the present invention will become manifest to those versed in the art upon making reference to the detailed description and the accompanying sheets of drawings in which a preferred structural embodiment incorporating the principles of the present invention is shown by way of illustrative example.

DETAILED DESCRIPTION OF THE PREFERRED EMBODIMENTS

The following descriptions are exemplary embodiments only, and are not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention as set forth in the appended claims.

Figure 1:
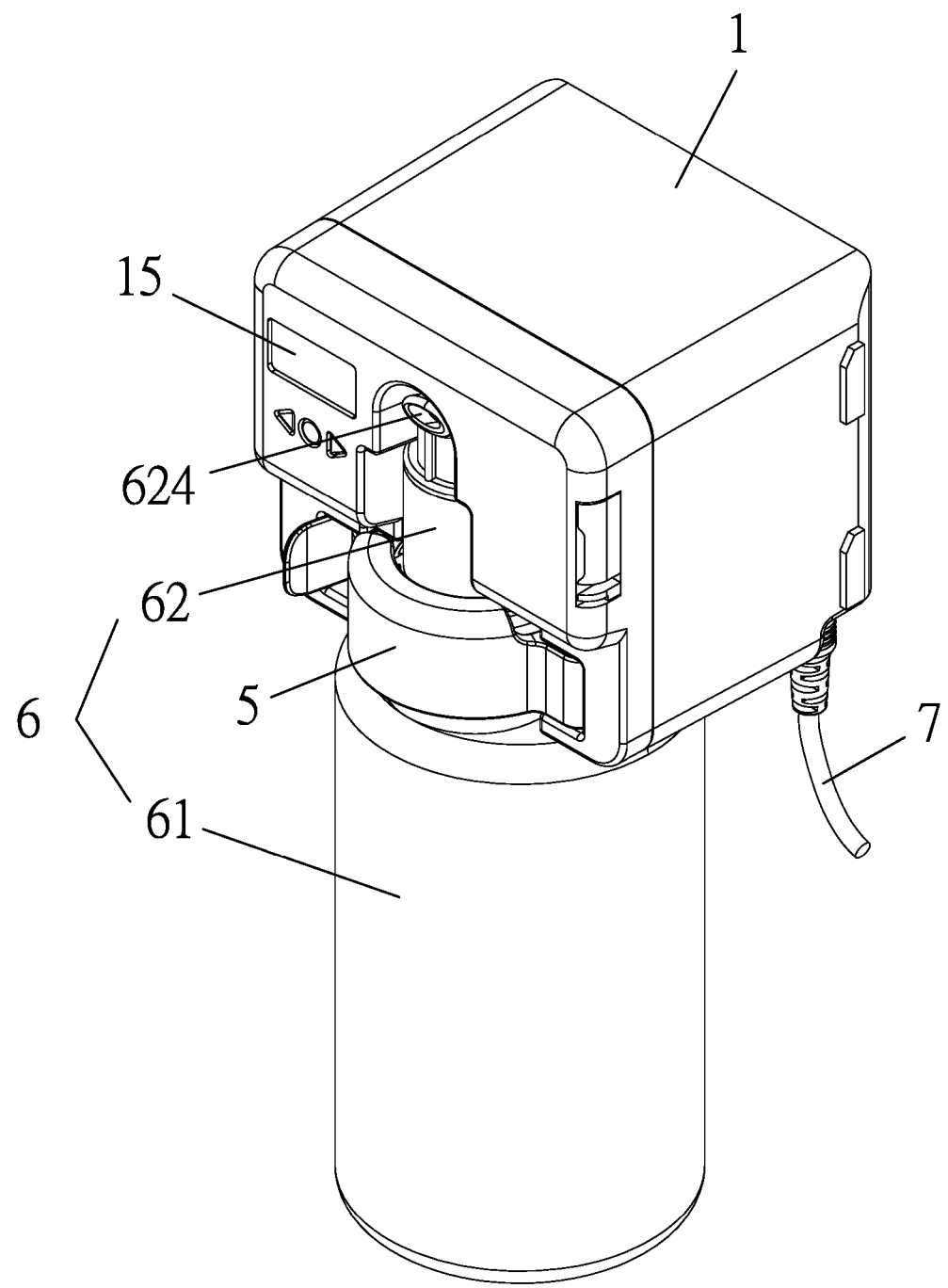
FIG. 1 is a perspective view of the present invention.
Figure 2:
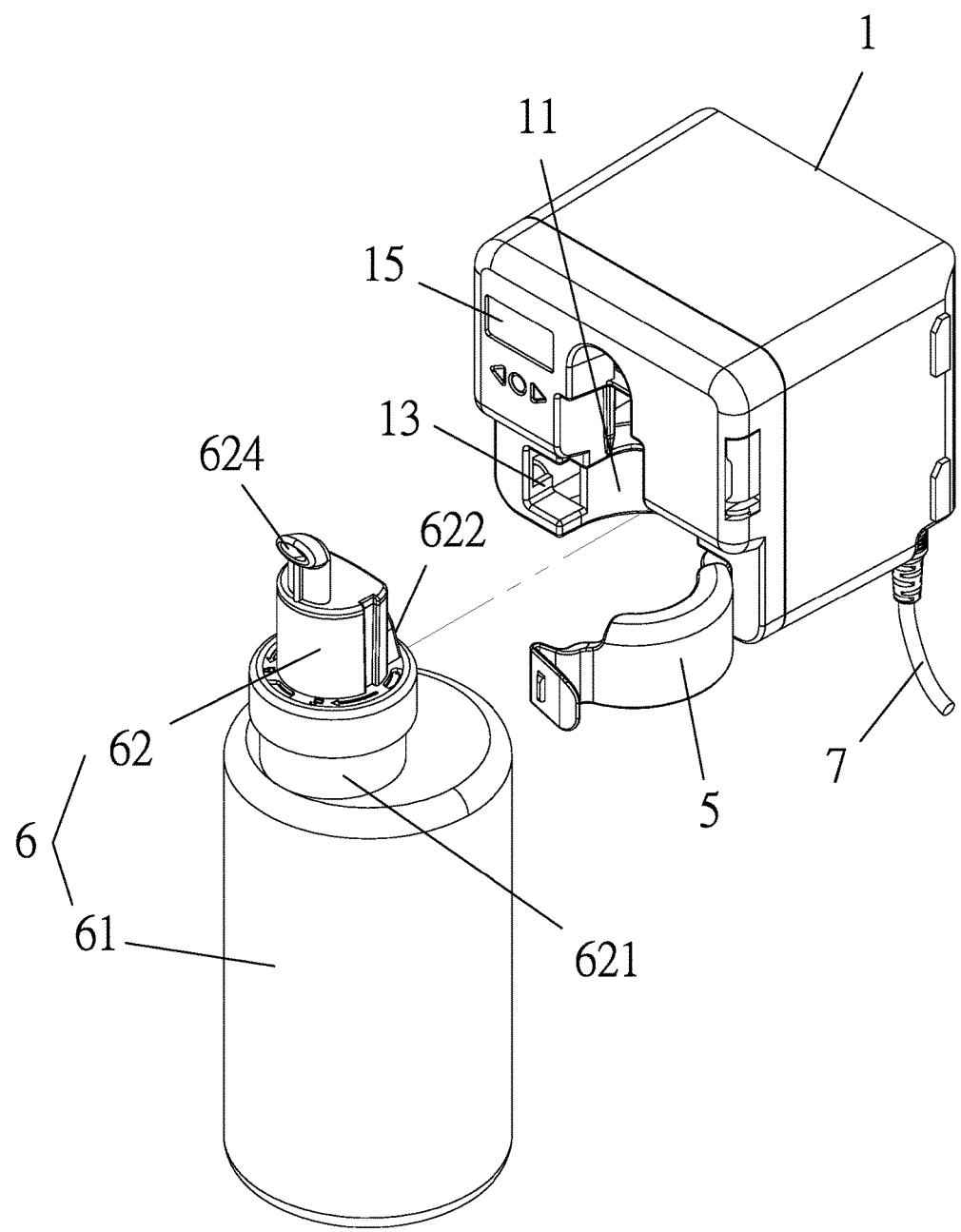
FIG. 2 is an exploded view of the present invention.
Figure 3:
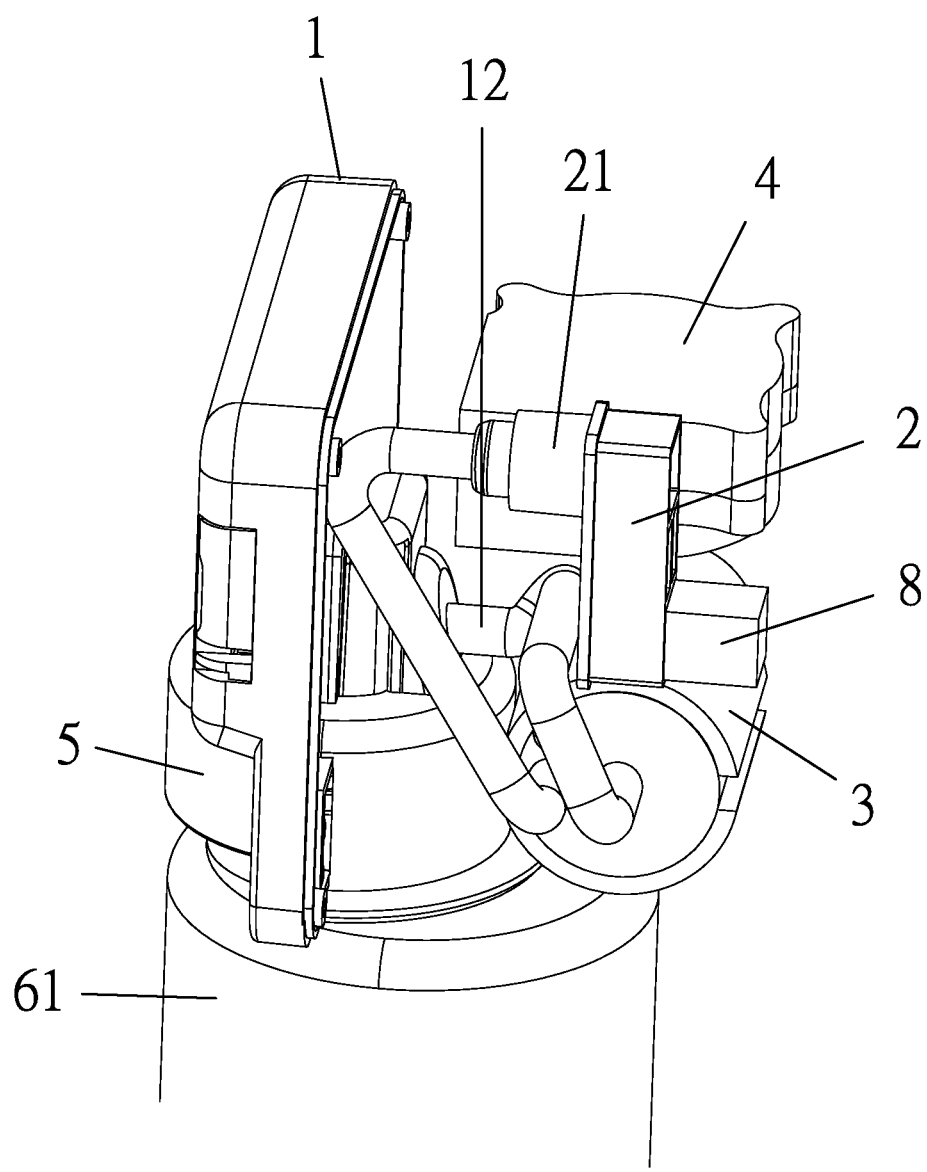
FIG. 3 is a schematic view illustrating inside details of a gas supply device of the present invention.
Figure 4:
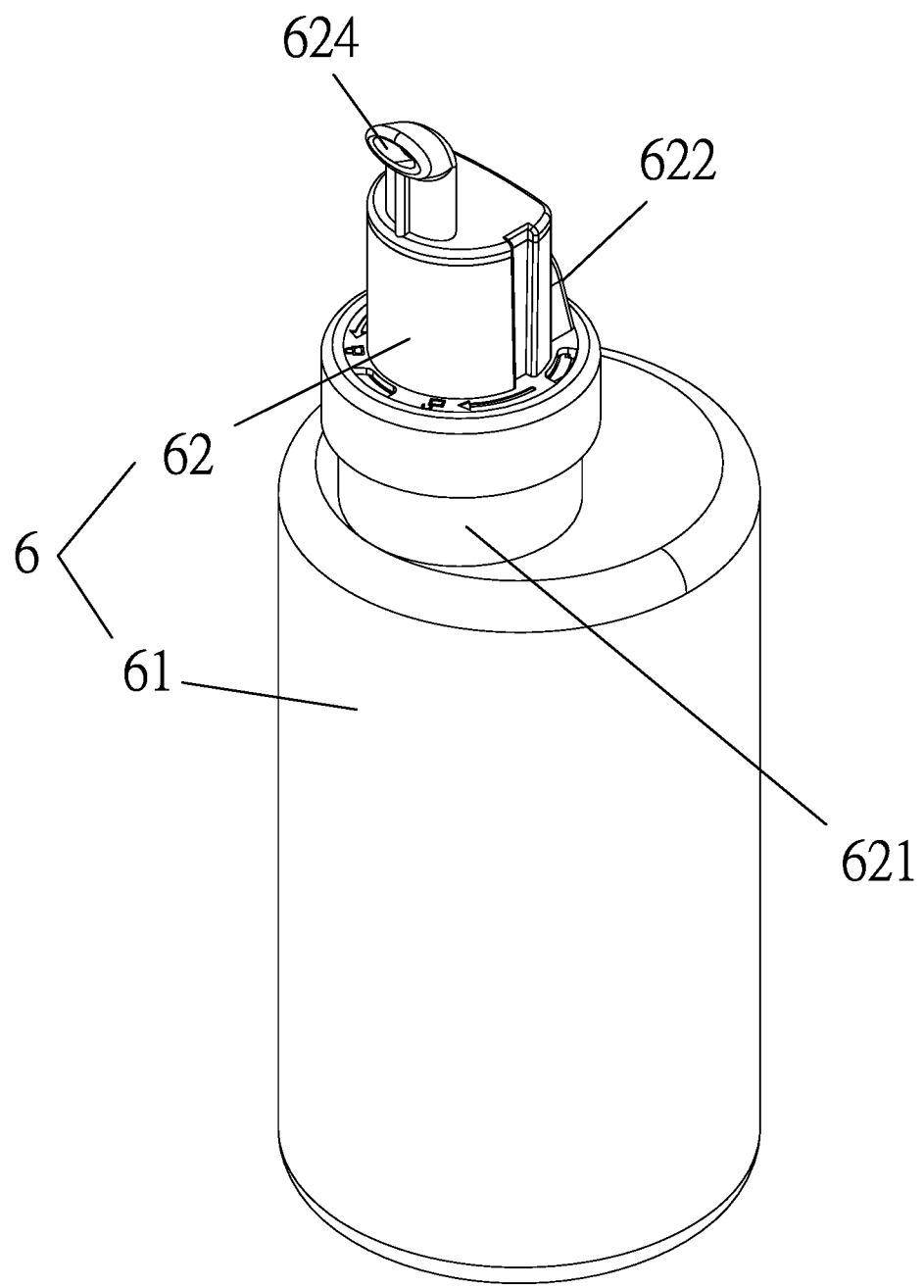
FIG. 4 is a perspective view, taking from a front side, of a diffusion device of the present invention.
Figure 5:
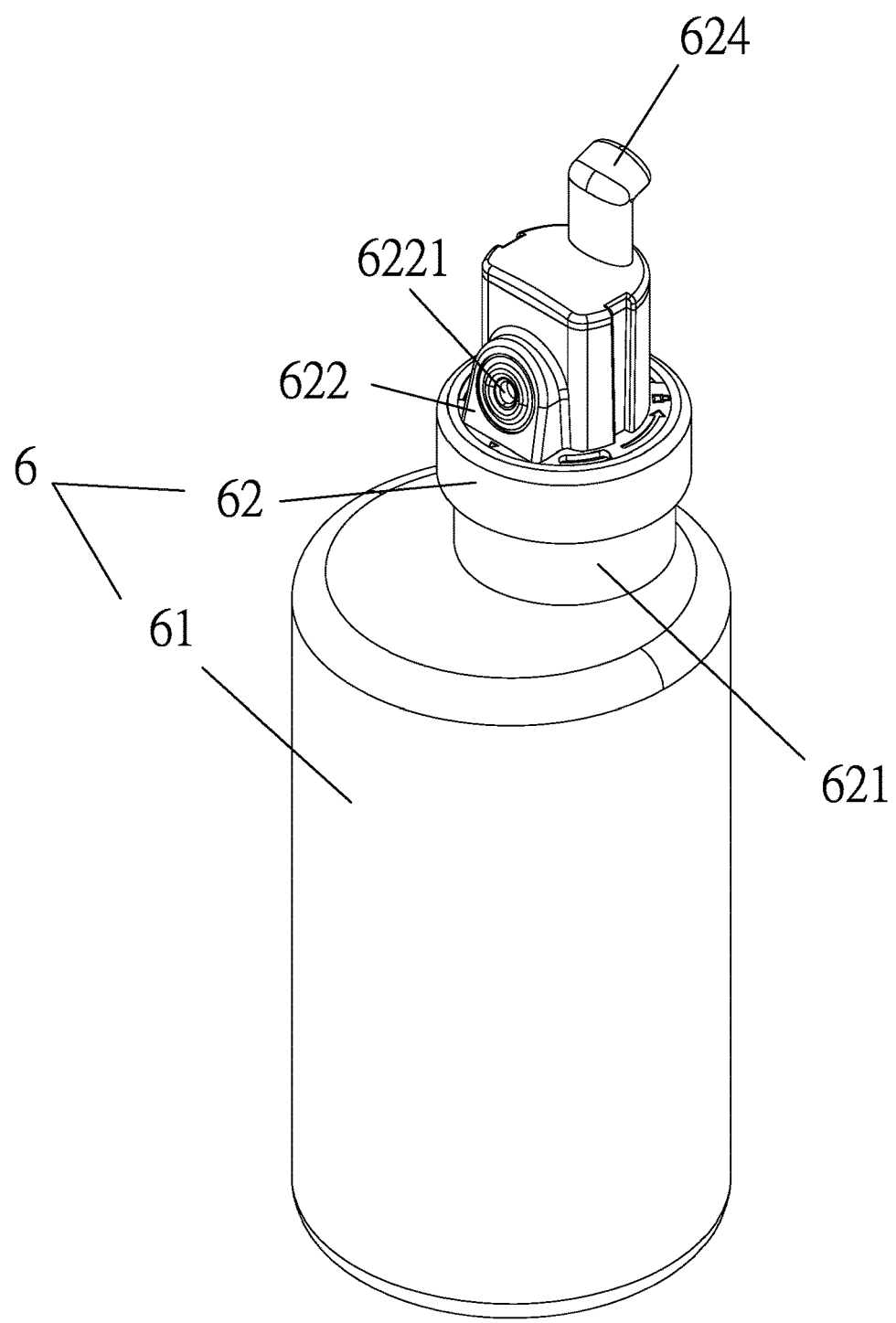
FIG. 5 is a perspective view, taking from a rear side, of the diffusion device of the present invention.
Figure 6:
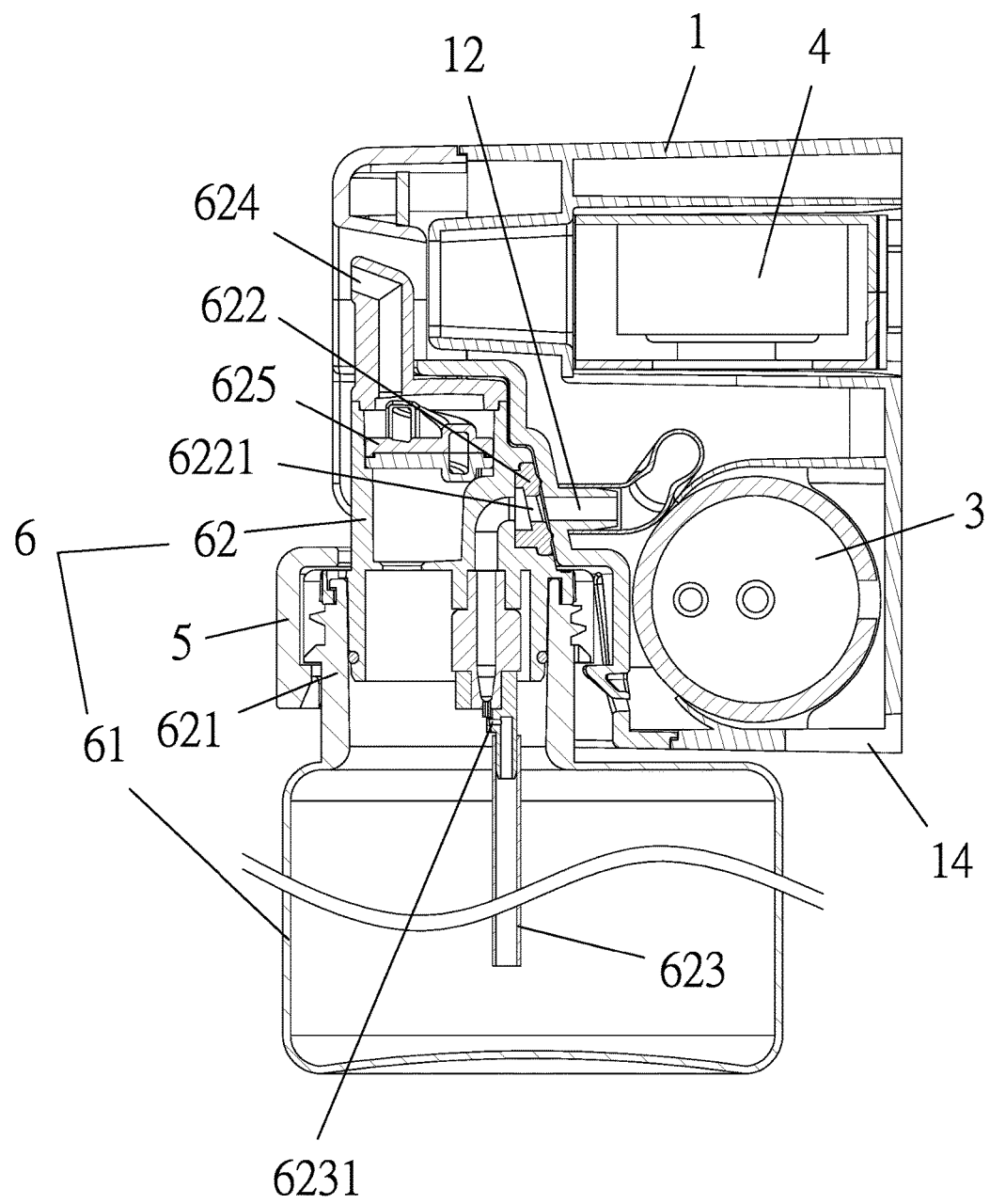
FIG. 6 is a cross-sectional view of the present invention.
Figure 7:
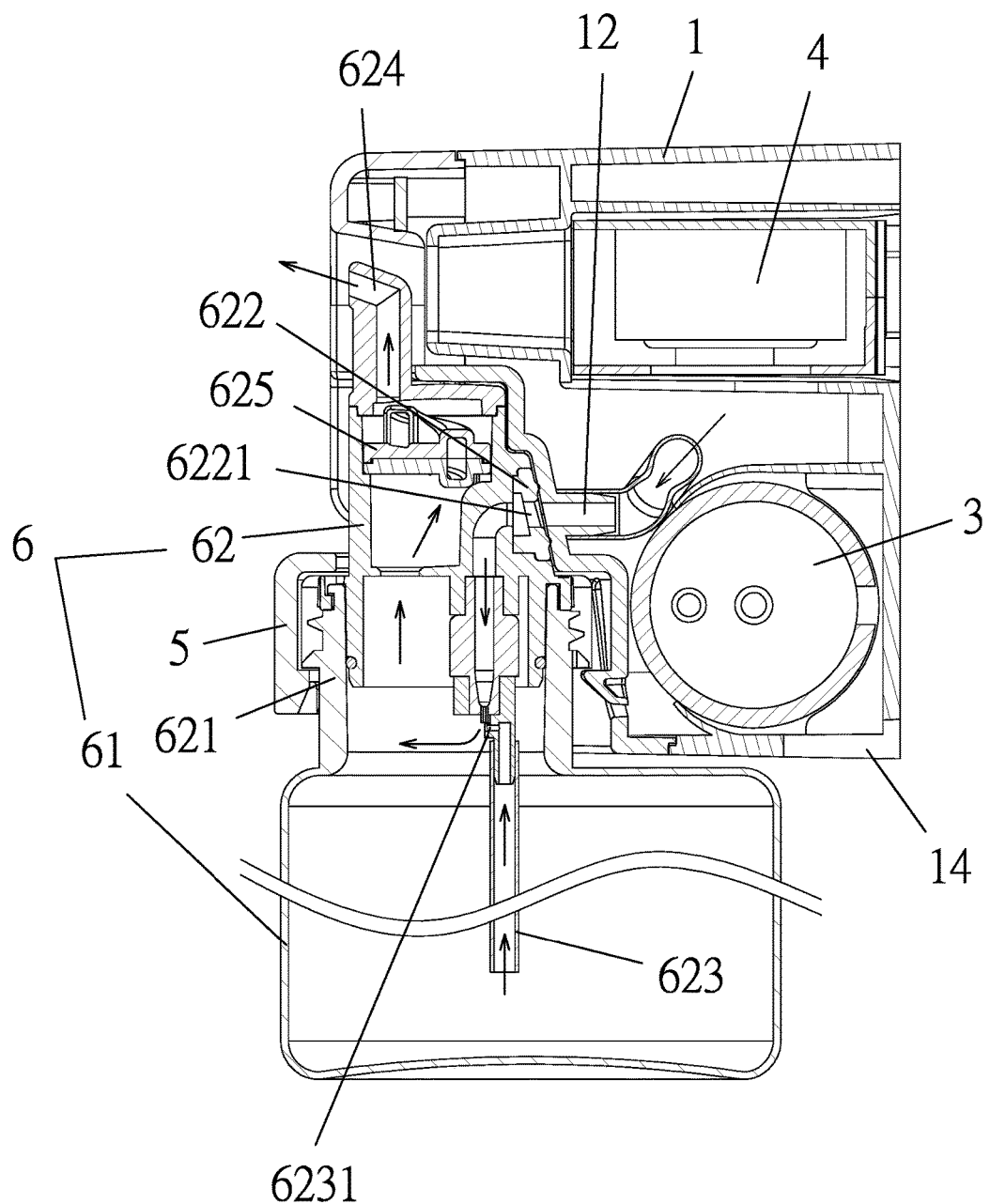
FIG. 7 is a schematic view illustrating a use condition of the present invention.
Figure 8:
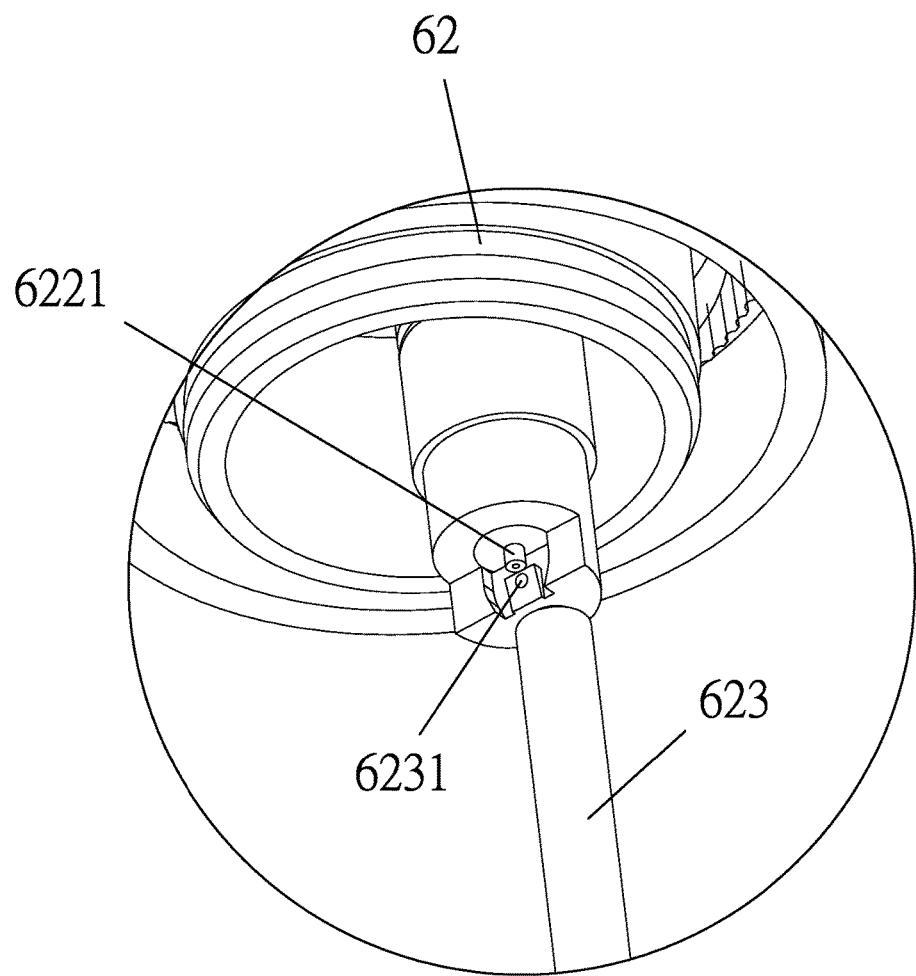
FIG. 8 is an enlarged view showing an atomization hole of the present invention.
Figure 9:
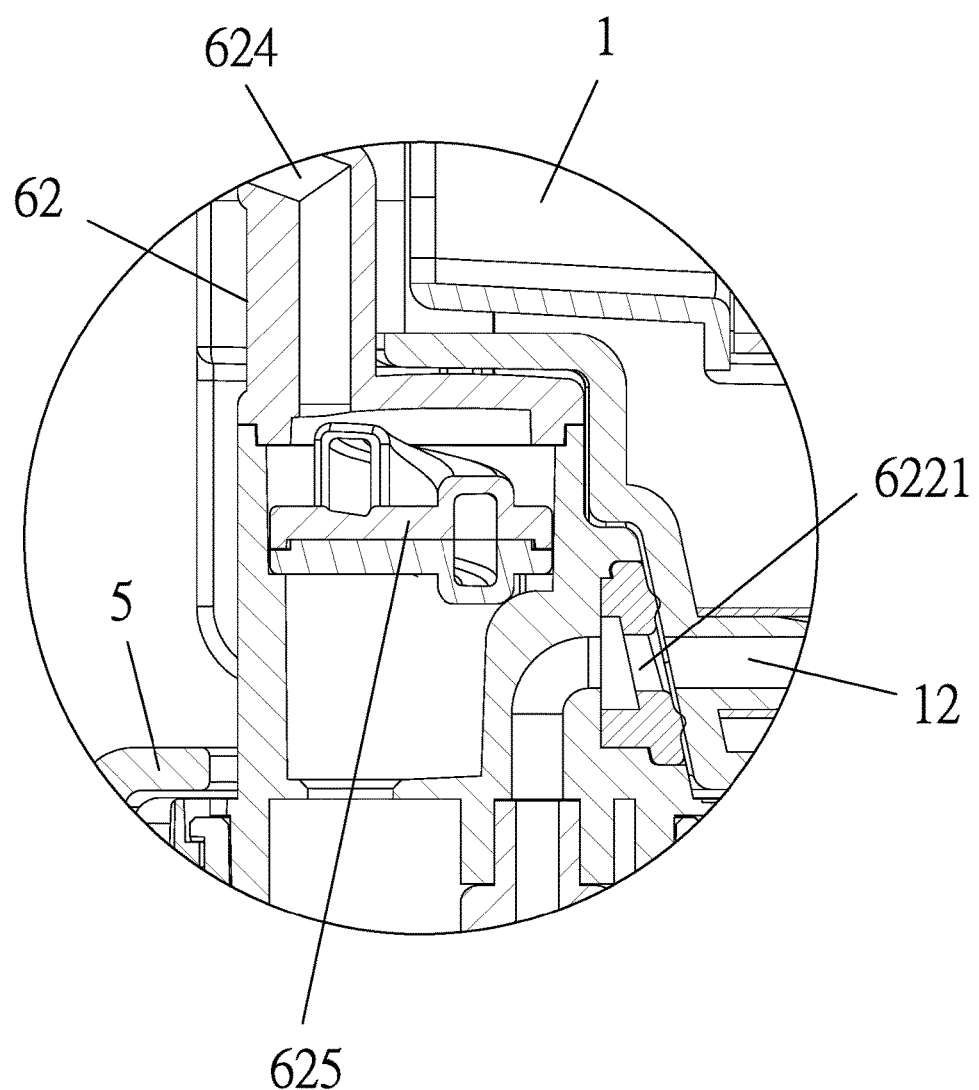
FIG. 9 is an enlarged view showing a slow flowing device of the present invention.
Figure 10:
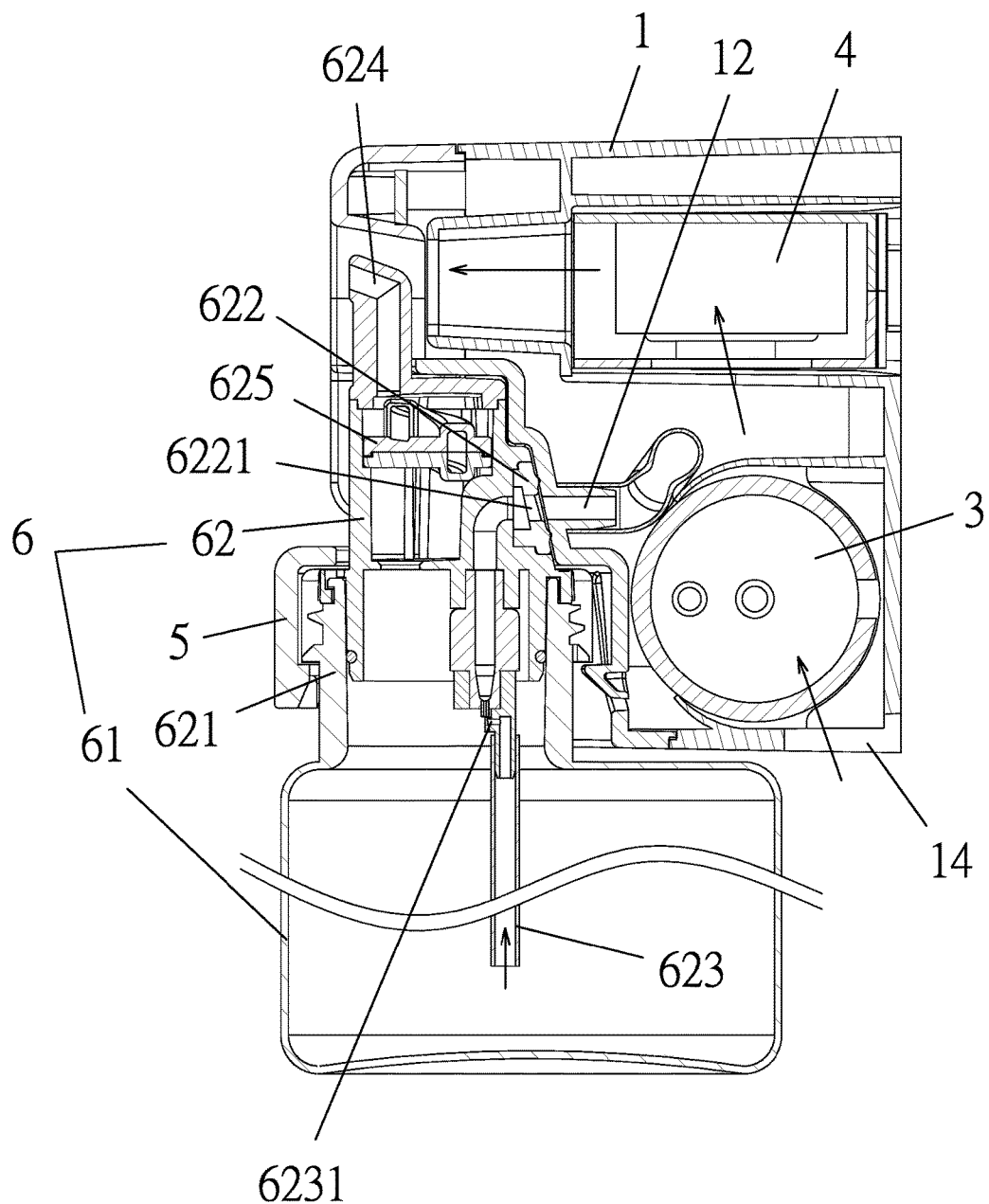
FIG. 10 is a schematic view illustrating a use condition of a flow driving device of the present invention.

Referring to FIGS. 1-6, which are respectively a perspective view of the present invention, an exploded view of the present invention, a schematic view illustrating inside details of a gas supply device of the present invention, a perspective view, taking from a front side, of a diffusion device of the present invention, a perspective view, taking from a rear side, of the diffusion device of the present invention, and a cross-sectional view of the present invention, as shown in the drawings, the present invention generally comprises a gas supply device 1, and the gas supply device 1 is provided therein with a gas inlet device 2, a compression element 3, and a flow driving device 4. The gas inlet device 2 comprises a gas inlet section (not shown) formed at one side thereof and a gas outlet section 21 formed at an opposite side thereof. The gas outlet section 21 has an end connected to the compression element 3. The gas supply device 1 is provided, on one side thereof, with a coupling section 11. The coupling section 11 is provided, in an inside thereof, with a gas conveyance hole 12. The gas conveyance hole 12 is connected to an end of the compression assembly 3. The coupling section 11 has a circumferential section that is coupled to a retention device 5. The retention device 5 has an end pivotally connected to the coupling section 11 and the coupling section 11 is provided, at an opposite side, with a retention trough 13 for engaging and retaining an opposite end of the retention device 5. The gas supply device 1 is provided, in a circumferential section thereof, with at least one air ingress opening 14, so that when the flow driving device 4 is in operation, external gas is first drawn in through the air ingress section 14 and then the gas is blown toward a side of the gas supply device 1. The gas supply device 1 is provided, on a side thereof, with a control section 15 so that the control section 15 is operable to control flowrate and time interval of gas spraying by the gas supply device 1.

Also included in a diffusion device 6, where the diffusion device 6 comprises a container 61 and a diffuser 62. The container 61 has an end connected to a circumference of the diffuser 62 so that a bottom of the diffuser 62 is received and held in an interior of the container 61. The diffuser 62 is provided, on the circumference thereof, with a retention section 621. The retention section 621 is engageable with and thus coupled to the retention device 5 to have the diffuser 62 clamped and retained between the retention device 5 and the coupling section 11. The diffuser 62 is provided, on the circumference thereof, with a gas entrance section 622. The gas entrance section 622 has a side that is provided with a gas entrance passage 6221. The gas entrance section 622 is a gas entrance section in the form of an inclined surface to facilitate mutual tight engagement between the gas entrance section 622 and the gas conveyance hole 12 so that the gas entrance passage 6221 is set in tight connection with the gas conveyance hole 12. The gas entrance passage 6221 has an end formed in a surface of the gas entrance section 622 and an opposite end of the gas entrance passage 6221 extends to a bottom of the diffuser 62 and an end of the gas entrance passage 6221 has a diameter that is greater than that of an opposite end of the gas entrance passage 6221. The diffuser 62 is provided, on the bottom thereof, with a liquid guiding device 623. The liquid guiding device 623 has an end connected to the bottom of the diffuser 62. The liquid guiding device 623 has an opposite end extending to a location adjacent to a bottom of the container 61. The liquid guiding device 623 is provided, in a circumference thereof, with an atomization hole 6231. The atomization hole 6231 has an end communicating with the liquid guiding device 623, while an opposite end of the atomization hole 6231 is arranged at a location adjacent to the opposite end of the gas entrance passage 6221. The diffuser 62 has a circumference that is coupled to the coupling section 11 and the gas conveyance hole 12 is in tight connection with the gas entrance passage 6221. The diffuser 62 is provided, in a top end thereof, with an exit opening 624. The diffuser 62 is provided, in the interior thereof, with a slow flowing device 625 for flowing down the flowing speed of pressurized gas and filtering off atomized objects having large particles to allow only fine atomized substance to spray out, thereby improving an effect of atomization.

In the above-described gas supply device 1, the gas supply device 1 is connected, at the circumference thereof, to an electrical wire 7 so that electrical power can be supplied through the electrical wire 7 to the gas supply device 1. Further, the gas supply device 1 is provided, in the interior thereof, with a power supply device (not shown) so that in case of power failure, the power supply may maintain continuous supply of electrical power to the gas supply device 1.

In the above-described gas inlet section, the gas inlet section is connected to a sponge 8 for filtering off impurities entraining external air.

In the above-described container 61, the container 61 receives and holds therein a liquid, and the liquid may comprises perfume, disinfection liquid, or insect expellant liquid.

Referring to FIGS. 2, 3, and 7-9, which are respectively an exploded view of the present invention, a schematic view illustrating inside details of the gas supply device of the present invention, a schematic view illustrating a use condition of the present invention, an enlarged view showing the atomization hole of the present invention, and an enlarged view showing the slow flowing device of the present invention, as shown in the drawings, the gas outlet section 21 is coupled to the compression element 3 and the compression element 3 is coupled to the gas conveyance hole 12 so that external gas, when drawn in through the gas inlet section of the gas inlet device 2, first passes through the sponge 8 for filtering and removal of impurities and then enters the interior of the gas inlet device 2 to be fed through the gas outlet section 21 into the compression assembly 3 to allow the compression assembly 3 to compress the gas to provide pressurized gas that is then fed to the gas conveyance hole 12. The gas conveyance hole 12 is in connection with the gas entrance passage 6221 and one end of the gas entrance passage 6221 is provided at the surface of the gas entrance section 622, while an opposite end extends to the bottom of the diffuser 62 so that the pressurized gas that is fed from the gas conveyance hole 12 to the gas entrance passage 6221 passes through the gas entrance passage 6221 to allow the pressurized gas to be introduced into the container 61. Further, due to the diameter of one end of the gas entrance passage 6221 is greater than that of another end so as to induce the Venturi effect, where the flow speed of a fluid that passes through a narrowed cross section would be increased and the pressure rises. As such, when the pressurized gas flows from one end of the gas entrance passage 6221 to the opposite end of the gas entrance passage 6221 and discharged therefrom, the flow speed and the pressure thereof would be increased. When the pressurized gas is introduced into the container 61, due to the opposite end of the gas entrance passage 6221 being adjacent to the atomization hole 6231, the pressurized gas flowing the location that is adjacent to the atomization hole 6231 would induce a negative pressure at such a site, such that the negative pressure zone induces a suction force due to the outside atmospheric pressure being relatively greater, whereby the liquid contained in the container 61 is sucked and drawn through the liquid guiding device 623 to the atomization hole 6231 and the liquid is then subjected to atomization by the atomization hole 6231 to have the liquid converted into atomized liquid.

Further, when the pressurized gas is introduced into the container 61, since the container 61 is a closed space, the pressurized gas is only allowed to flow out through the exit opening 624. When the pressurized gas flows toward the exit opening 624, the atomized liquid is also driven thereby to the exit opening 624, whereby the pressurized gas and atomized liquid are fed out. Further, the slow flowing device 625 helps increase the time interval that is necessary for the pressurized gas to flow to the exit opening 624 in order to prevent the situation where the liquid is just atomized while the pressurized gas has already fed out through the exit opening 624 and also functions to filter off large particles of the atomized gas, allowing only fine particles to be discharged so as to make better atomization. In this way, automatic spraying can be achieved effectively.

When the pressurized gas and the atomized liquid are discharged through the exit opening 624, the flow driving device 4 simultaneously drives gas that is drawn in from the outside through the air ingress section 14 toward one side of the gas supply device 1 so as to blow the atomized liquid to a further location, making the atomized liquid spread to a further location, where the term "further location" is such that for atomized liquid that is driven out by the pressurized gas to cover a distance of for example one meter, the flow driving device 4 so arranged to blow the external gas to the atomized gas would help spread the atomized liquid to cover a range more than one meter in distance.

It will be understood that each of the elements described above, or two or more together may also find a useful application in other types of methods differing from the type described above.

While certain novel features of this invention have been shown and described and are pointed out in the annexed claim, it is not intended to be limited to the details above, since it will be understood that various omissions, modifications, substitutions and changes in the forms and details of the device illustrated and in its operation can be made by those skilled in the art without departing in any way from the claims of the present invention.

I claim:

1. A disposable gas diffusion device, comprising:

a gas supply device, which is provided, in an interior thereof, with a gas inlet device and a compression element, the gas inlet device being provided, at one side thereof, with a gas inlet section and being also provided, at another side thereof, with a gas outlet section, the gas outlet section having an end connected to the compression element, the gas supply device being provided, at one side thereof, with a coupling section, the coupling section being provided, in an inside thereof, with a gas conveyance hole, the gas conveyance hole being connected to one end of the compression element; and a diffusion device, which is connected to the coupling section, the diffusion device comprising a container and a diffuser, the container having an end connected to a circumference of the diffuser to allow a bottom of the diffuser to be received in an interior of the container, the diffuser having a circumference that is provided with a gas entrance section, the gas entrance section having one side that is provided with a gas entrance passage, the gas entrance passage being in tight connection with the gas conveyance hole, the gas entrance passage having an end arranged at a side of the gas entrance section, the gas entrance passage having another end extending to a bottom of the diffuser, the diffuser being provided, in the bottom thereof, with a liquid guiding device, the liquid guiding device having an end connected to the bottom of the diffuser, the liquid guiding device having another end extending to a location adjacent to a bottom of the container, the liquid guiding device having a circumference in which an atomization hole is formed, the atomization hole having an end communicating with the liquid guiding device, the atomization hole having another end arranged at a location adjacent to another end of the gas entrance passage, the diffuser having a circumference connected to the coupling section, the gas conveyance hole being in tight connection with the gas entrance passage, the diffuser having a top end that is provided with an exit opening;

wherein the gas supply device is provided, in an interior thereof, with a flow driving device, the gas supply device having a circumference that is provided with at least one air ingress opening, whereby when the flow driving device is put in operation, external gas is first drawn in through the air ingress opening and the gas is then blown to one side of the gas supply device so that gas fed out through the exit opening is blown further by the gas blown out of the flow driving device.

2. The disposable gas diffusion device according to claim 1, wherein the coupling section has a circumference that is connected to a retention device, the retention device has an end pivotally connected to one side of the coupling section, the retention device having another end engaging and retained by another side of the coupling section to retain the diffuser between the coupling section and the retention device.

3. The disposable gas diffusion device according to claim 2, wherein the coupling section is provided, in another side, with a retention trough for engaging and retaining another end of the retention device.

4. The disposable gas diffusion device according to claim 2, wherein the diffuser has a circumference that is provided with a retention section, the retention section being in engagement with and retained by the retention device to have the diffuser retained between the retention device and the coupling section.

5. The disposable gas diffusion device according to claim 2, wherein the diffuser is provided, in an interior thereof, with a slow flowing device for reducing a speed of a pressurized gas and filtering off large particles of atomized liquid.

6. The disposable gas diffusion device according to claim 1, wherein the gas supply device is provided, on one side thereof, with a control section so that the control section controls flow rate and time interval of spraying gas by the gas supply device.

7. The disposable gas diffusion device according to claim 1, wherein the gas supply device has a circumference to which an electrical wire is connected so that electrical power is supplied through the electrical wire to the gas supply device and the gas supply device is provided, in an interior thereof, with a power supply device so that the power supply device supplies electrical power to the gas supply device in case of power failure.

8. The disposable gas diffusion device according to claim 1, wherein the gas entrance section is a gas entrance section in the form of an inclined surface to facilitate tight connection between the gas entrance section and the gas conveyance hole so that the gas entrance passage is kept in tight connection with the gas conveyance hole.

9. The disposable gas diffusion device according to claim 8, wherein the gas entrance passage has one end having a diameter that is greater than a diameter of another end of the gas entrance passage.

10. The disposable gas diffusion device according to claim 1, wherein the gas inlet section is coupled to a sponge for filtering off impurities entraining external air.

11. The disposable gas diffusion device according to claim 1, wherein the container receives and holds therein a liquid and the liquid comprises perfume, disinfection liquid, or insect expellant liquid.

12. The disposable gas diffusion device according to claim 4, wherein the diffuser is provided, in an interior thereof, with a slow flowing device for reducing a speed of a pressurized gas and filtering off large particles of atomized liquid.

13. The disposable gas diffusion device according to claim 6, wherein the gas supply device has a circumference to which an electrical wire is connected so that electrical power is supplied through the electrical wire to the gas supply device and the gas supply device is provided, in an interior thereof, with a power supply device so that the power supply device supplies electrical power to the gas supply device in case of power failure.

* * * * *